US008696640B2

(12) United States Patent
Churchill

(10) Patent No.: US 8,696,640 B2
(45) Date of Patent: Apr. 15, 2014

(54) SNAKE VENOM EVACUATION AND MEDICATION INJECTION DEVICE

(76) Inventor: Russell Churchill, Phoenix, AZ (US)

( * ) Notice: Subject to any disclaimer, the term of this patent is extended or adjusted under 35 U.S.C. 154(b) by 372 days.

(21) Appl. No.: 12/987,288

(22) Filed: Jan. 10, 2011

(65) Prior Publication Data

US 2012/0179092 A1    Jul. 12, 2012

(51) Int. Cl.
*A61M 1/00* (2006.01)
*A61M 37/00* (2006.01)

(52) U.S. Cl.
USPC ............... 604/314; 604/35; 604/27; 604/319; 604/500

(58) Field of Classification Search
USPC .............. 604/314, 35, 318, 319, 500, 27
See application file for complete search history.

(56) References Cited

U.S. PATENT DOCUMENTS

| 1,221,103 | A | | 4/1917 | Sorensen | |
|---|---|---|---|---|---|
| 1,864,700 | A | | 6/1932 | Wade | |
| 1,960,889 | A | * | 5/1934 | Benedict | 604/314 |
| 2,360,051 | A | | 10/1944 | Eweson | |
| 2,539,846 | A | * | 1/1951 | Lewis et al. | 417/555.1 |
| 2,701,559 | A | * | 2/1955 | Cooper | 600/569 |
| 3,068,868 | A | * | 12/1962 | Skopyk | 604/314 |
| 3,115,138 | A | * | 12/1963 | McElvenny et al. | 604/133 |
| 3,125,094 | A | * | 3/1964 | Krug | 604/314 |
| 3,477,437 | A | * | 11/1969 | Goldberg | 604/117 |
| 3,625,217 | A | * | 12/1971 | Schmidt | 604/314 |
| 3,683,922 | A | * | 8/1972 | Cutter | 604/314 |
| 3,742,954 | A | | 7/1973 | Strickland | |
| 3,752,158 | A | * | 8/1973 | Kariher | 604/133 |
| 4,128,173 | A | * | 12/1978 | Lazarus et al. | 206/570 |
| 4,246,899 | A | * | 1/1981 | Loseff | 604/97.02 |
| 5,387,203 | A | | 2/1995 | Goodrich | |
| 5,415,182 | A | * | 5/1995 | Chin et al. | 600/567 |
| 5,886,003 | A | * | 3/1999 | Cohen et al. | 514/280 |
| 7,758,518 | B2 | * | 7/2010 | Perez et al. | 600/583 |
| 7,841,991 | B2 | * | 11/2010 | Douglas et al. | 600/583 |
| 7,931,651 | B2 | * | 4/2011 | Webb et al. | 606/59 |
| 8,062,272 | B2 | * | 11/2011 | Weston | 604/313 |
| 2002/0077584 | A1 | * | 6/2002 | Lin et al. | 604/21 |
| 2003/0069553 | A1 | * | 4/2003 | Talamonti | 604/314 |
| 2004/0078063 | A1 | * | 4/2004 | McLaren | 607/46 |
| 2005/0085769 | A1 | * | 4/2005 | MacMahon et al. | 604/96.01 |
| 2007/0270710 | A1 | * | 11/2007 | Frass et al. | 600/567 |
| 2008/0097154 | A1 | * | 4/2008 | Makower et al. | 600/114 |
| 2008/0103361 | A1 | * | 5/2008 | Makower et al. | 600/115 |
| 2008/0281156 | A1 | * | 11/2008 | Makower et al. | 600/118 |
| 2008/0306436 | A1 | * | 12/2008 | Edwards et al. | 604/67 |
| 2008/0306456 | A1 | * | 12/2008 | Riesinger | 604/316 |
| 2012/0226192 | A1 | * | 9/2012 | McClellan | 600/567 |

* cited by examiner

*Primary Examiner* — Emily Schmidt
*Assistant Examiner* — Michael J Anderson
(74) *Attorney, Agent, or Firm* — Venable, Campillo, Logan & Meaney, P.C.

(57) ABSTRACT

A device for treating a snake bite wound that utilizes a hypodermic tube with a curvature that is similar to a typical snake fang whereby the hypodermic tube on one end comprises a smooth bulbous tip with at least one opening and a vacuum source is attached to the other end of the hypodermic tube. The tip is inserted into a snake bite wound, and due to the curved shape of the hypodermic tube, the tip and the tube then follow the curved shape of the snake bite wound without damaging any of the tissue surrounding the snake bite canal. The vacuum source then extracts any venom that is present from the wound. The device also enables medicine to be injected into the wounded area to treat the wound.

22 Claims, 1 Drawing Sheet

SNAKE VENOM EVACUATION AND MEDICATION INJECTION DEVICE

BACKGROUND OF THE INVENTION

The present invention relates generally to the treatment of snake bites, but may be useful in treating other types of venomous bites and in particular, the need to treat snake bites by both extracting snake venom from a victim's wound, and injecting medication such as antivenin or antibiotics to effectively treat the Patient to help reduce the possibility of death, tissue death, discomfort, infection, or disfigurement.

The prior art contains devices that allow people to extract snake venom from a wounded area. For example, the invention described in U.S. Pat. No. 3,742,954 includes a lance and telescopically-mounted poison extractor tube in a single unit. The lance includes two blades mounted on a spring member that is released by a trigger arrangement, which allows the lance to cut into a person's flesh at a given length. Once the lance is inserted to open the wounded area, the lance is then removed so that the poison may be extracted. This is accomplished by placing the tube over the wound so that a person can create suction by sucking air through a hole on one side of the tube.

Another example of the representative prior art is described in U.S. Pat. No. 2,539,846. The patent discloses a pump with a piston construction connected to a nozzle with a small open tip whereby the tip is placed over the wounded area and the pumping mechanism extracts any snake venom from within the flesh.

In a similar manner, U.S. Pat. No. 5,387,203 discloses a device that uses a syringe-like structure for extracting pus, blood, and other materials from beneath a person's skin. The device uses a plunger that is pulled out through a tube to create a vacuum when the tube is placed securely on top of the person's skin. The vacuum pulls the skin area into the tube so that it can be punctured by a piercing element, thereby allowing the blood, pus, or other materials to be extracted from the skin area and into the tube. U.S. Pat. No. 3,625,217 operates in a similar fashion without the use of a piercing device.

Finally, it is also generally known that a standard hypodermic needle and syringe may be used to pierce and extract the venom directly from the wounded area.

Advantageously, all of these devices enable a snake bite victim to treat the wound by extracting the snake's venom using various forms of simple suction and lancing techniques.

SUMMARY OF THE INVENTION

When a snake bites its victim, the trauma to the affected area can be severe and requires immediate treatment to minimize tissue and nerve damage, the spread of the poisonous venom to other areas of the body, and prevent the victim from losing consciousness or even dying. The problem is further exacerbated when a victim is in a wilderness area where competent medical treatment is either primitive or non-existent.

A typical snakebite will create a venom cavity or vacuole within the tissue. If the toxin in the venom cavity is left untreated, the body will eventually absorb the venom into the surrounding tissue and the venom will enter the blood or lymph streams or both. In these cases, the quick and efficient removal of the venom from the wound can be the difference between life and death.

While the prior art devices are designed to remove the venom directly from the wound, these devices are not efficient, and many times, not effective at treating a snake bite. In particular, the devices that utilize vacuum suction techniques often create bulging and hemorrhaging to the entry site of the wound. As a result, the dermal and subcutaneous tissue layers, as well as the muscle tissues damaged by the vacuum can lead to edema. This often will close the wound's opening and prevent any opportunity to extract venom from the subcutaneous tissue.

Furthermore, because snake fangs are curved, they do not pierce tissue in a straight line. When a standard straight hypodermic needle and syringe are used to extract venom from the wounded area, the needle cannot track the curved shape of the wound and is too sharp to follow the wound cavity. This means that while the needle may ultimately reach the venom cavity, the needle will likely inflict damage to the surrounding area. By doing so, the surrounding tissue will likely absorb the venom more quickly. Also, because the depth of a snake bite varies, it is also difficult to determine how deep to insert a standard needle, and there is no way to be certain the needle opening is ideally located in the center of the wound cavity.

In addition to inflicting damage to the surrounding tissue, the prior art snake bite treatments offer no way to deliver high concentrations of medicine such as antivenin or antibiotics directly into the tissue immediately surrounding the wound without further damaging the tissue or creating other pathways for the venom to enter the blood stream. Initially, the bite site is where the highest concentration of venom exists. The need to get the medicine to the area of highest venom concentrations as quickly as possible is crucial. A hemotoxic venom will quickly cause the tissue nearest the wound to begin necrosis or coagulopathy. If antivenin, antibiotics, or other medications are not delivered quickly to the wound, a number of serious complications may arise such as ecchymosis, rhabdomyolysis leading to hyperkalemia or possibly severe edema causing compartment syndrome. One treatment for compartment syndrome requires cutting the skin and muscle fascia lengthwise down the limb to allow the muscles to expand consistent with the blood flow. This type of treatment inevitably leaves an unsightly scar. In addition, some patients require high doses of antivenin to counteract the effects of the venom especially in localized areas, it may induce a condition called serum sickness which may cause signs and symptoms consistent with an allergic reaction, which may sometimes be severe. The treatment protocol is to give only as much antivenin as is required.

These problems and shortcomings of the prior art are overcome with the present invention. The invention provides a way to both effectively and efficiently extract snake venom from a snake bite wound and deliver the necessary medicinal substances without damaging the surrounding tissue. The preferred embodiment of the invention accomplishes this by using a hypodermic tube connected to a vacuum source such that the tube has a curvature that conforms, or is shaped to the curvature of a snake fang. Preferably, the tube comprises either a metal hypodermic needle or a plastic catheter. The vacuum source may comprise some form of a syringe, vacuum bottle, or any device capable of generating a gentle suction. The tip should preferably be smooth and bulbous with one or more openings so that the tube can slide easily into the wound canal and reach the venom cavity directly without damaging the surrounding tissue. When the tip reaches the bottom of the venom cavity, the tip's smooth texture and bulbous shape would preclude the device from being inserted any further. The vacuum source can then draw the venom out of the cavity through the openings in the tip, flow up the tube, and into a reservoir.

The tube also provides a way to deliver medication directly to the wound. Presuming the tube is inserted in the same manner as just described; the syringe, intravenous dripper (I.V.) or pump delivery system can deliver the medication directly to the wounded area and be absorbed through the same tissue pathways as the venom. The invention gives the added advantage of immediately neutralizing the venom's toxicity at the exact point of delivery, before the venom can migrate and necrotize other tissues within the body. One benefit of the process is the potential reduction in the amount of antivenin required to treat the patient, thereby reducing the risk of serum sickness.

The description of the invention which follows, together with the accompanying drawings should not be construed as limiting the invention to the example shown and described, because those skilled in the art to which this invention appertains will be able to devise other forms thereof within the ambit of the appended claims.

DESCRIPTION OF AN EMBODIMENT

Figure 1:
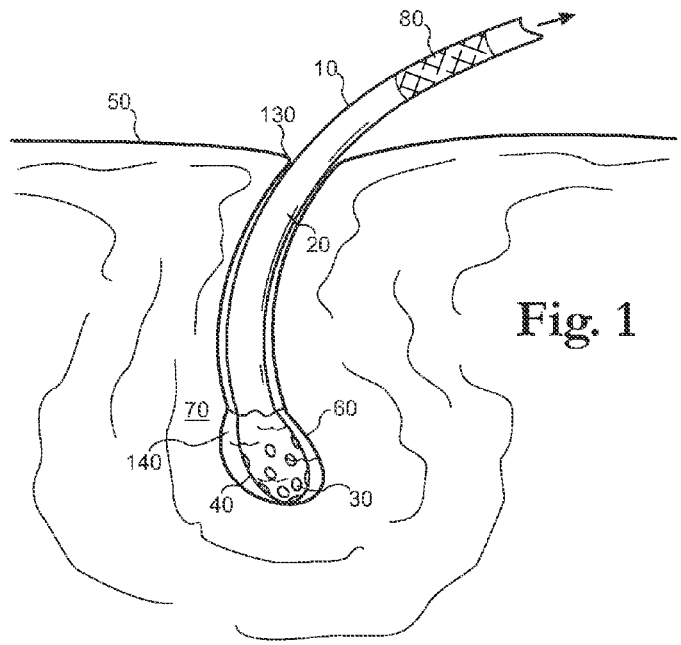
FIG. 1 is a cross-sectional view of the tube shown in a fully-inserted position into a snake bite wound.

By way of one example of many to serve as background in understanding the preferred embodiment of the present invention, as shown in FIG. 1, is a device for extracting snake venom 10 from a bite victim. The extracting device includes a hypodermic tube 20 for inserting into a human flesh wound and tissue 70. It is understood by those in the art that the device could work equally as well on animal bite wounds. The tube preferably comprises either a curved metal hypodermic needle or a plastic catheter. The tube 20 is integrated with a hollow bulbous tip 40 such that the tube 20 has a curvature that is similar to the curvature of a typical snake fang. Preferably, the tip 40 should be smooth and bulbous such that the diameter of the tip 40 may be greater than that of the tube 20. A grip 80 for holding the device 10 may be secured to, or integrated with the tube 20. By utilizing a tube 20 with a typical snake-fang-shaped curvature and a smooth bulbous tip 40, the tube 20 may penetrate the entry point 130 of a snake bite and follow the contour of the wound without damaging the outer layer of skin 50 or the tissue 70 that surrounds the location of the wound. The grip 80 should rest at a point far enough away from the tip 40 so that the grip 80 does not obstruct the tip 40 from reaching the venom vacuole 60 when the tip is inserted into the tissue 70. The tip 40 preferably should contain one or more holes 30.

Figure 2:
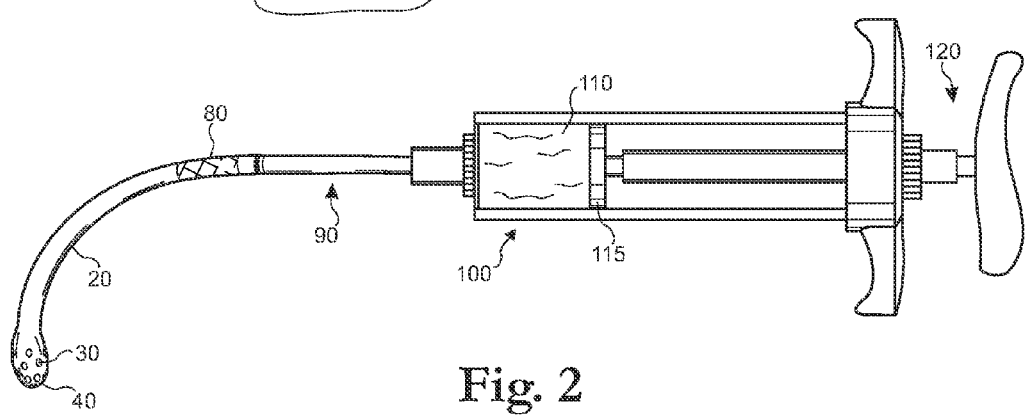
FIG. 2 is a side view of the tube with the syringe acting as a vacuum source.

As shown in FIG. 2, the tube 20 is attached to one end of a delivery tube 90. A syringe or similar vacuum device 100 is secured to the other end of the delivery tube either directly or by means of a flexible hose 90. When the plunger 120 of the syringe 100 is pulled outward, a vacuum is formed within the syringe container 110. When a vacuum suction is applied to the tube 20, the venom 140 is drawn from a venom vacuole 60 into the holes 30. The venom 140 travels up the tube 20, through the delivery tube 90, and into the container 110 of the syringe 100.

After extracting the venom 140 from the venom vacuole 60, the device 10 may be used to deliver medicines to the venom vacuole 60. To do so, medicine such as antivenin or antibiotics in liquid form 115 are placed in the syringe container, I.V. or medical grade pump 110. The plunger 120 is then pushed down thereby forcing the liquid 115 from the syringe 100 into the delivery tube 90 and into the tube 20. Once in the tube 20, the medicine 115 travels into the tip 40 and out the holes 30 where it reaches the venom vacuole 60. It is understood by those of ordinary skill in the art that the medicine 115 will travel similar pathways to the venom to be absorbed by the surrounding tissue 70 where it will immediately treat the envenomated area.

Figure 3:
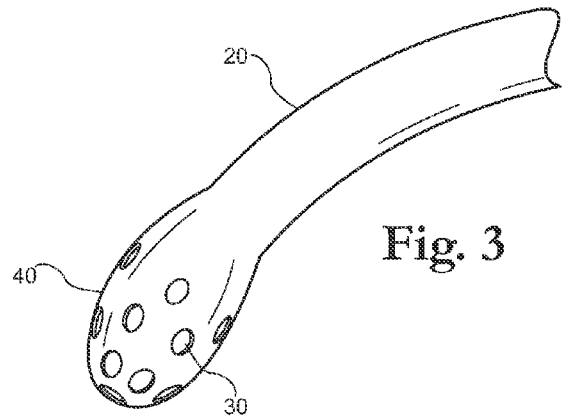
FIG. 3 is a side view and close up view of the tube.

A more detailed view of the tip of the needle is shown in FIG. 3.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

Although the invention has been described in detail with reference to one or more particular preferred embodiments, persons possessing ordinary skill in the art to which this invention pertains will appreciate that various modifications and enhancements may be made without departing from the spirit and scope of the claims that follow.

What is claimed is:

1. A device for both extracting venom from a snake bite wound and delivering medicine to the wound comprising:
   a hypodermic tube;
   a hollow tip;
      the hollow tip comprises a diameter that is different than the diameter of the hypodermic tube and is integrated with one end of the hypodermic tube and;
      the hollow tip further comprises multiple openings such that a fluid flows through the openings either from, or into the hypodermic tube;
   the hypodermic tube having a curvature that enables the hypodermic tube to follow a curved path of a snake bite wound when the tip of the device is inserted into the snake bite wound.

2. The device of claim 1 further comprising a vacuum source whereby the vacuum source is connected to a second end of the hypodermic tube.

3. The device of claim 1 such that the hollow tip is bulbous.

4. The device of claim 1 such that the hollow tip further comprises a smooth plastic material.

5. The device of claim 1 such that the hypodermic tube is a metal hypodermic needle.

6. The device of claim 1 such that the hypodermic tube is a plastic catheter.

7. The device of claim 1 further comprising a grip such that the grip is attached to the hypodermic tube above the hollow tip.

8. The device of claim 2 such that the vacuum source is a syringe.

9. The device of claim 2 such that the vacuum source is an evacuated container.

10. The device of claim 2 such that the vacuum source is a medical grade pump.

11. A method of extracting venom from a snake bite wound comprising the steps of:
   inserting a hollow tip of a device into the snake bite wound until the hollow tip enters a venom vacuole within the snake bite wound whereby the hollow tip is connected to one end of a curved hypodermic tube;
   applying a vacuum source to a second end of the hypodermic tube such that the vacuum source draws a venom deposit from the venom vacuole into the hollow tip through multiple openings in the hollow tip.

12. The method of claim 11 wherein the vacuum source is a syringe.

13. The method of claim 11 such that the hollow tip is bulbous.

14. The method of claim 11 such that the hollow tip further comprises a smooth plastic material.

15. The method of claim 11 such that the hypodermic tube is a metal hypodermic needle.

16. The method of claim 11 such that the hypodermic tube is a plastic catheter.

17. A method of delivering medication to a snake bite wound comprising the steps of:
    inserting a hollow tip of a device into the snake bite wound until the hollow tip enters a venom vacuole within the snake bite wound whereby the hollow tip is connected to one end of a curved hypodermic tube;
    injecting the medication into a second end of the hypodermic tube such that the medication moves from the hypodermic tube into the venom vacuole through multiple openings in the hollow tip.

18. The method of claim 17 wherein the medication is inserted into the hypodermic tube using a syringe.

19. The method of claim 17 such that the hollow tip is bulbous.

20. The method of claim 17 such that the hollow tip further comprises a smooth plastic material.

21. The method of claim 17 such that the hypodermic tube is a metal hypodermic needle.

22. The method of claim 17 such that the hypodermic tube is a plastic catheter.

\* \* \* \* \*